US011911259B2

(12) United States Patent
Gorochow

(10) Patent No.: US 11,911,259 B2
(45) Date of Patent: Feb. 27, 2024

(54) MULTI-LAYER FOLDING FLOW DIVERTERS

(71) Applicant: DePuy Synthes Products, Inc., Raynham, MA (US)

(72) Inventor: Lacey Gorochow, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 238 days.

(21) Appl. No.: 17/369,014

(22) Filed: Jul. 7, 2021

(65) Prior Publication Data

US 2022/0031443 A1 Feb. 3, 2022

Related U.S. Application Data

(60) Provisional application No. 63/059,524, filed on Jul. 31, 2020.

(51) Int. Cl.
A61B 17/12 (2006.01)
A61F 2/02 (2006.01)
(Continued)

(52) U.S. Cl.
CPC .......... *A61F 2/06* (2013.01); *A61B 17/12109* (2013.01); *A61B 17/12177* (2013.01);
(Continued)

(58) Field of Classification Search
CPC ................. A61F 2/06; A61F 2002/068; A61F 2002/823; A61F 2002/821;
(Continued)

(56) References Cited

U.S. PATENT DOCUMENTS 5,980,552 A * 11/1999 Pinchasik ............... A61F 2/856
623/1.16
10,076,428 B2 9/2018 Gorochow
(Continued)

FOREIGN PATENT DOCUMENTS

DE 10 2007 012964 A1 9/2008
WO 2011/023105 A1 3/2011
WO 2013/065040 A1 5/2013

OTHER PUBLICATIONS

International Search Report issued in International Patent Application No. PCT/IB2021/056874 dated Nov. 11, 2021.

*Primary Examiner* — Shaun L David
*Assistant Examiner* — Mitchell Brian Hoag
(74) *Attorney, Agent, or Firm* — TROUTMAN PEPPER HAMILTON SANDERS LLP

(57) ABSTRACT

A tubular, folding flow diverter is provided. The flow diverter includes a plurality of sections, including a first section, a second section, and a third section. The flow diverter is shapeable to an elongated cylindrical shape and is (Continued)

movable to an implanted configuration. In the implanted configuration, the second section and at least a portion of the first and third sections overlap to form a three-layer shape. This three-layer shape can be positioned proximate an aneurysm neck when implanted in a patient. The overall porosity of the implant can be higher than legacy implants, because the overlapping portion of the three sections can decrease the porosity proximate the aneurysm neck.

16 Claims, 8 Drawing Sheets

(51) Int. Cl.
    *A61F 2/06*     (2013.01)
    *A61F 2/95*     (2013.01)
    *A61F 2/07*     (2013.01)
    *A61F 2/82*     (2013.01)

(52) U.S. Cl.
    CPC ............ *A61F 2/95* (2013.01); *A61B 17/12113* (2013.01); *A61F 2002/068* (2013.01); *A61F 2/07* (2013.01); *A61F 2/82* (2013.01); *A61F 2002/823* (2013.01); *A61F 2002/9534* (2013.01)

(58) Field of Classification Search
    CPC ................. A61F 2002/825; A61F 2/07; A61F 2002/072; A61F 2002/075; A61F 2/2418; A61F 2/82; A61F 2/844; A61B 17/12109; A61B 17/12113
See application file for complete search history.

(56) References Cited

U.S. PATENT DOCUMENTS

| | | | |
|---|---|---|---|
| 2004/0117007 A1* | 6/2004 | Whitbourne | A61L 31/10 623/1.42 |
| 2008/0200945 A1* | 8/2008 | Amplatz | A61B 17/0057 606/213 |
| 2009/0043371 A1* | 2/2009 | Fearnot | A61F 2/07 623/1.13 |
| 2009/0062841 A1* | 3/2009 | Amplatz | A61B 17/12159 606/200 |
| 2010/0305686 A1* | 12/2010 | Cragg | A61F 2/07 623/1.35 |
| 2014/0288635 A1* | 9/2014 | Shalev | A61F 2/82 623/1.16 |
| 2014/0324154 A1* | 10/2014 | Shalev | A61F 2/82 623/1.13 |
| 2014/0358178 A1* | 12/2014 | Hewitt | A61B 17/12172 606/200 |
| 2014/0364930 A1* | 12/2014 | Strauss | A61B 17/1214 623/1.11 |
| 2018/0110637 A1* | 4/2018 | Kealey | A61L 27/06 |
| 2020/0015953 A1* | 1/2020 | Caplice | A61B 17/3417 |
| 2021/0137671 A1* | 5/2021 | Walzman | A61F 2/852 |

* cited by examiner

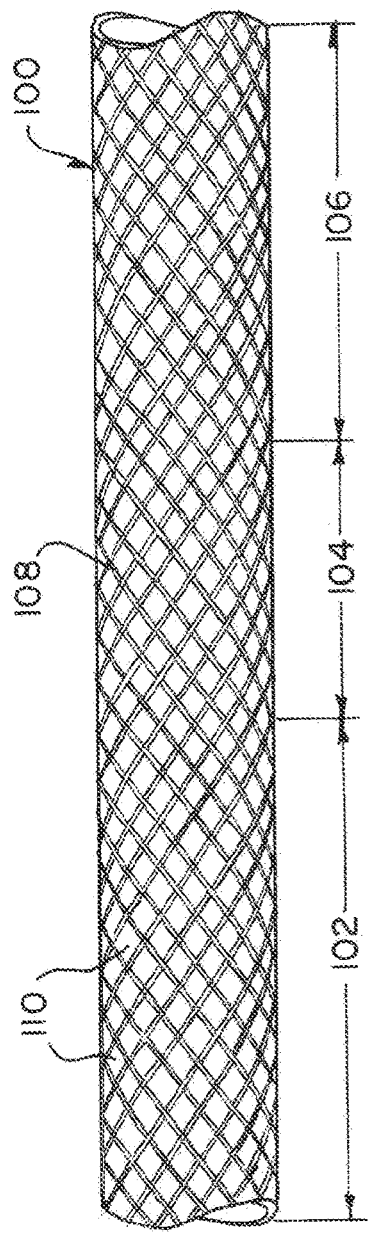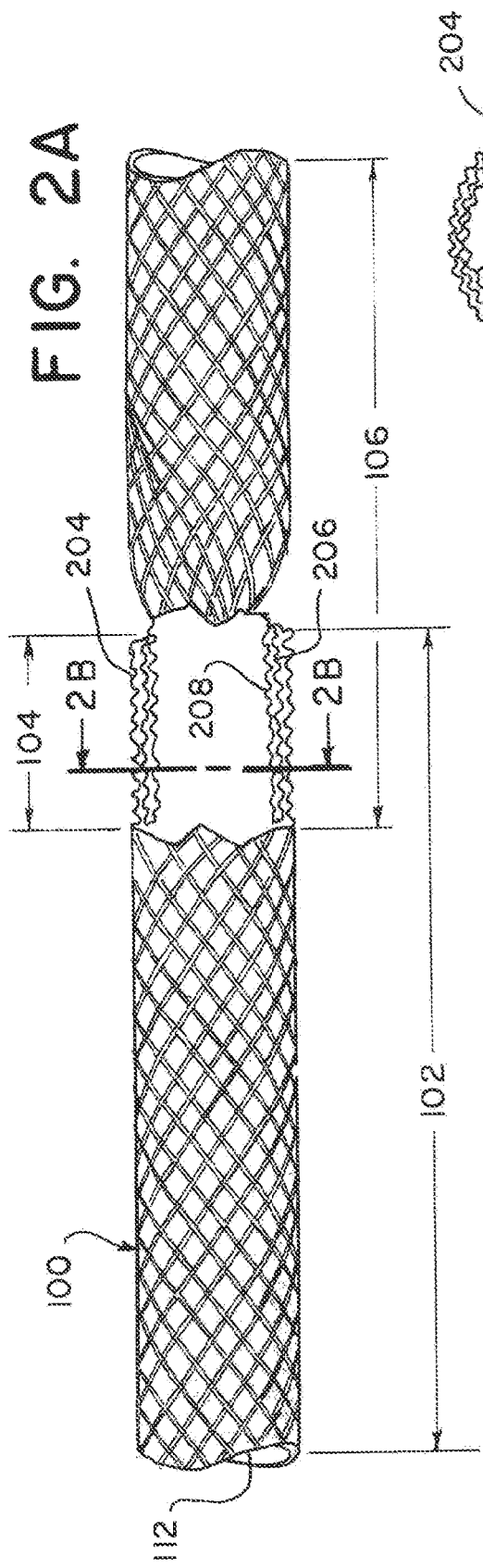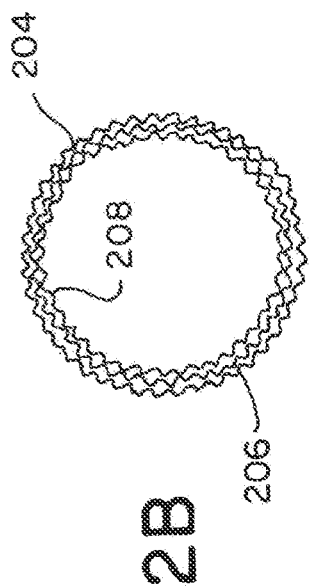

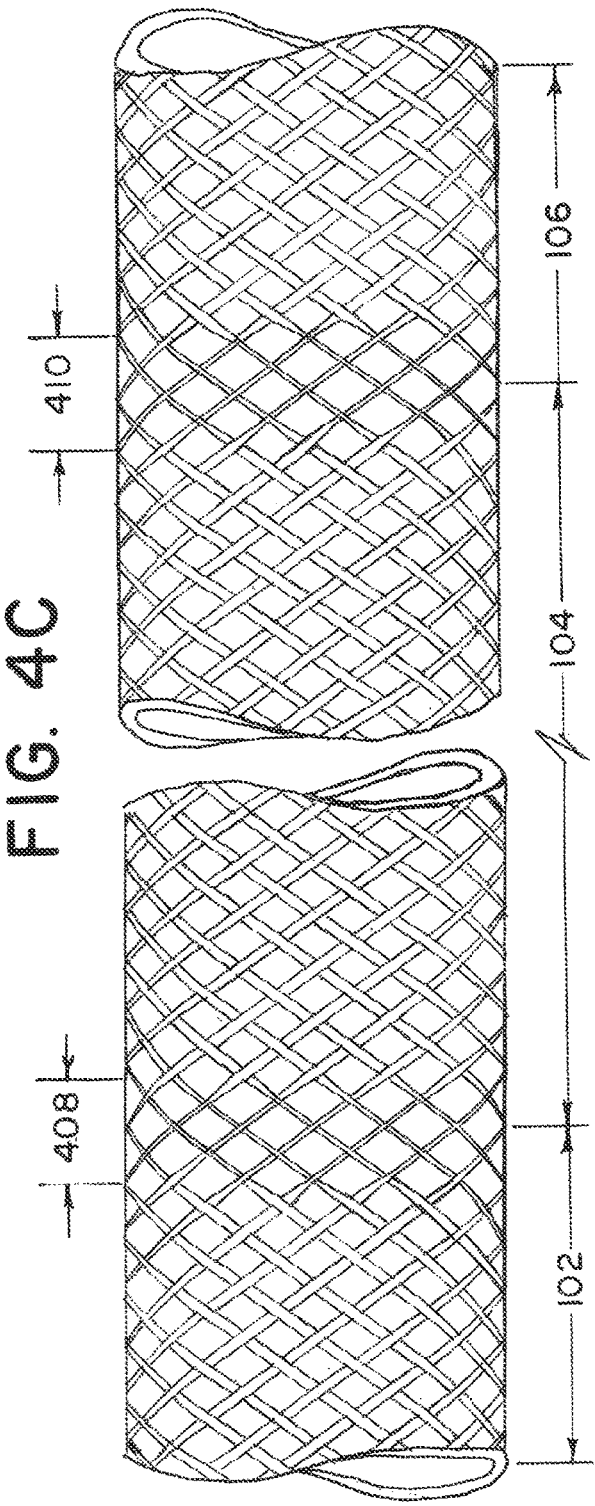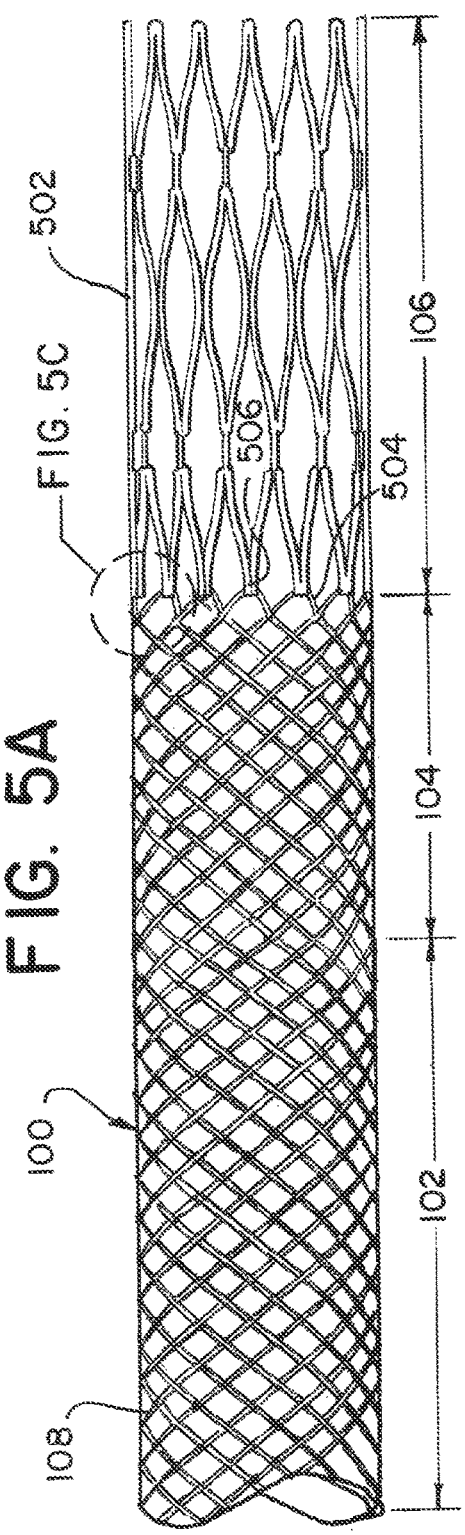

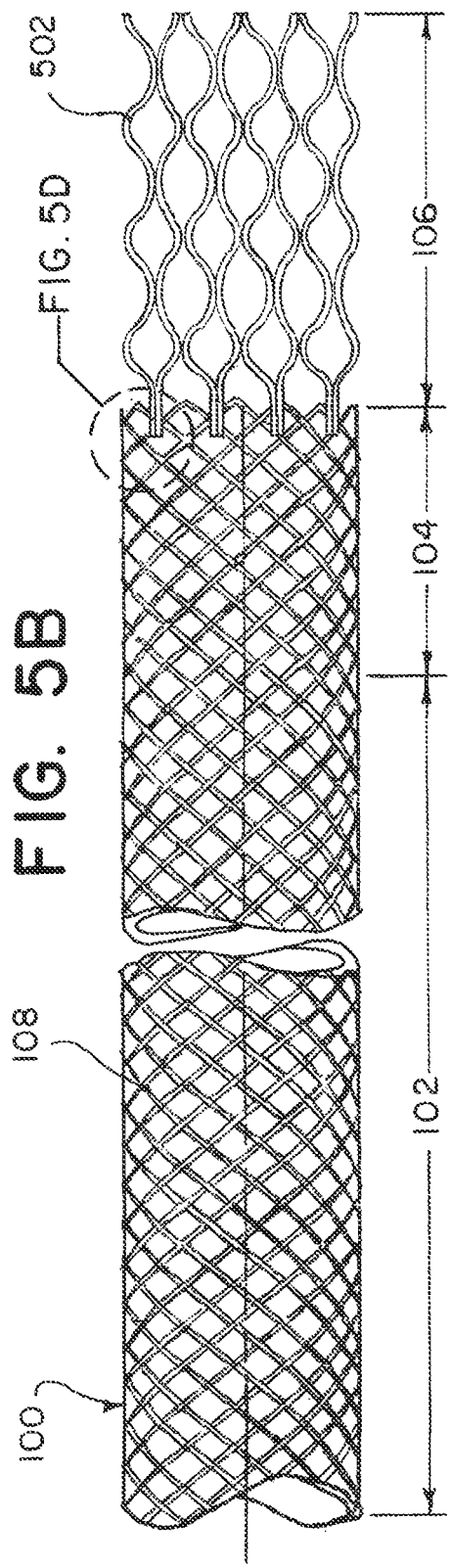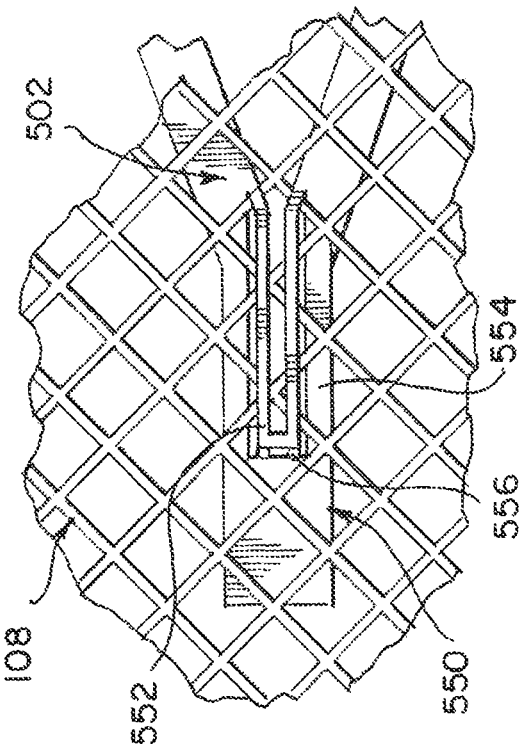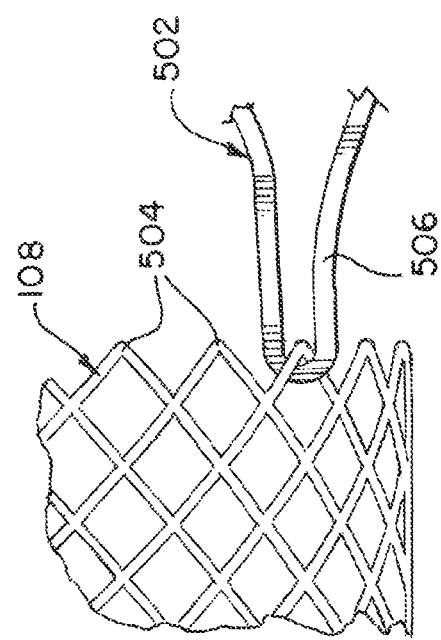

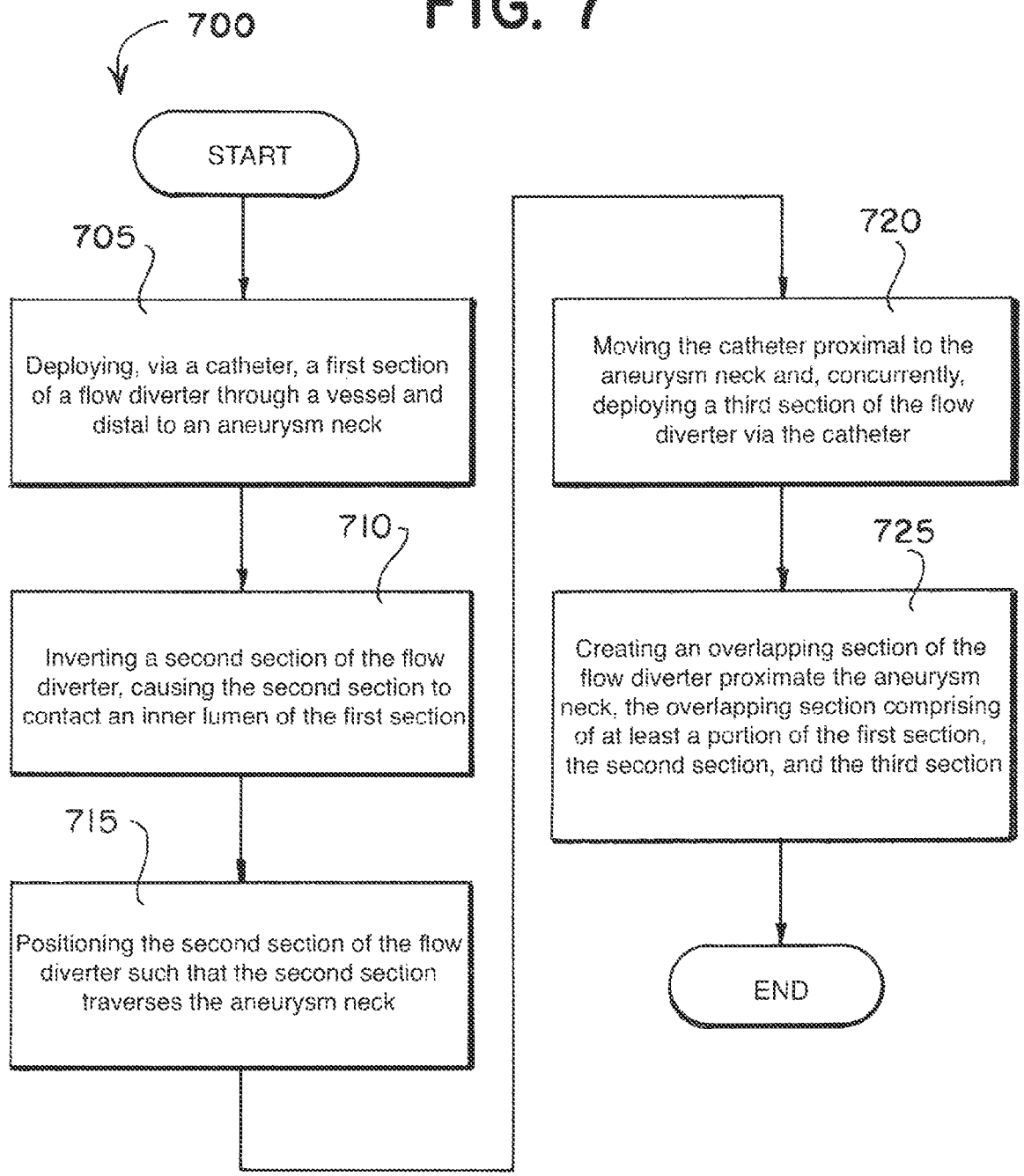

MULTI-LAYER FOLDING FLOW DIVERTERS

CROSS REFERENCE TO RELATED APPLICATION

This application claims priority, and benefit under 35 U.S.C. § 119(e), to U.S. Provisional Patent Application No. 63/059,524, filed 31 Jul. 2020, which is incorporated herein by reference as if fully set forth below.

FIELD OF INVENTION

The present invention generally relates to medical devices, and more particularly, to embolic implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include intravascularly delivered treatment devices that fill the sac of the aneurysm with embolic material or block the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current intravascularly delivered devices typically utilize multiple embolic coils to either fill the sac or treat the entrance of the aneurysm. Naturally formed thrombotic masses formed by treating the entrance with embolic coils can result in improved healing compared to aneurysm masses packed with embolic coils, because naturally formed thrombotic masses can reduce the likelihood of distention from arterial walls and facilitate reintegration into the original parent vessel shape along the neck plane. However, embolic coils delivered to the neck of the aneurysm can potentially have the adverse effect of impeding the flow of blood in the adjoining blood vessel, particularly if the entrance is overpacked. Conversely, if the entrance is insufficiently packed, blood flow can persist into the aneurysm. Treating certain aneurysm morphology (e.g. wide neck, bifurcation, etc.) can require ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, blood flow, or large aneurysm size.

Alternatives to embolic coils are being explored, for example in the form of tubular braided flow diverters. Braided flow diverters typically include braided material that acts to slow down blood flow into the aneurysm to clot off the aneurysm. The braided material typically consists of a single layer of 48-96 wires in order to exhibit a 70% porous structure. A porosity of 70% has been clinically proven to be dense enough to treat the aneurysm, yet porous enough to not occlude side branching vessels. This type of braid can be difficult to deliver in a microcatheter, however, especially in highly tortuous anatomy. This can be attributed to the overall porosity of the braid itself, as a 70% porous braid still contains 30% material by volume and is thus relatively stiff.

There is therefore a need for improved methods, devices, and systems for flow diverters that are able to occlude an aneurysm while, at the same time, are easily deployed through a microcatheter.

SUMMARY

It is an object of the present invention to provide systems, devices, and methods to meet the above-stated needs. Generally, it is an object of the present invention to provide a vascular flow diverter that can be delivered in a delivery configuration and folded into an implanted configuration. The vascular flow diverter can have a first tubular section defining an inner lumen. A third tubular section can be positionable within the inner lumen of the first tubular section. A second tubular section can be positioned between the first and third tubular section. In the delivery configuration, the first tubular section, the second tubular section, and the third tubular section can define a single-layer cylindrical shape. In the implanted configuration, the second tubular section can be overlapped by at least a portion of the first tubular section and the third tubular section, thereby creating a three-layer shape proximate the second tubular section.

The porosity of the first tubular section, the third tubular section, and the second tubular section can be higher than the porosity of prior braided mesh designs. For example, the first tubular section, the third tubular section, and the second tubular section can be a braided mesh comprising a porosity of from approximately 80% to approximately 90%.

When the vascular flow diverter is in the implanted configuration, the three-layer shape proximate the second tubular section can have a porosity of from approximately 50% to approximately 70%. As described above, a porosity of 70% or less has been clinically proven to be dense enough to treat the aneurysm.

In some examples, the second tubular section can have a different porosity than the first tubular section and the third tubular section.

The first tubular section, the third tubular section, and the second tubular section can each include a braided mesh. The braided mesh of the second tubular section can have a different braid angle than the braided mesh of the first tubular section and the third tubular section.

The second tubular section can have a first material thickness, and the first tubular section and the third tubular section can have a second material thickness. The first material thickness can be less than the second material thickness.

A first inflection point can be positioned between first tubular section and the second tubular section, and a second inflection point can be positioned between third tubular section and the second tubular section. The inflection points can help facilitate the folding from the delivery configuration to the implanted configuration.

One of the first tubular section and the third tubular section can include a braided mesh. The other of the third tubular section and the first tubular section can include a laser cut stent.

The second tubular section can include an anti-thrombogenic coating. The coating proximate the aneurysm can help prevent in-implant stenosis.

Another object of the present invention is to provide an implant shapeable to a cylindrical shape and movable to an implanted shape. The implant can include a first section having a first outer layer. The implant can include a second section having a second outer layer foldable to contact the first outer layer. The implant can include a third section comprising a third outer layer foldable to contact the second outer layer. When in the implanted shape, the implant can have a three-layer overlapping section including the first outer layer, the second outer layer, and the third outer layer. When in the implanted shape, the three-layer overlapping section can be positioned proximate an aneurysm neck.

The second section can include a braided mesh having a porosity of from approximately 80% to approximately 90%. When in the implanted shape, the three-layer overlapping section can have a porosity of from approximately 50% to approximately 70%.

The first section, the third section, and the second section can each include a braided mesh. The braided mesh of the second section can have a different braid angle than the braided mesh of the first section and the third section.

The implant can include a first inflection point positioned between first section and the second section. The implant can include a second inflection point positioned between third section and the second section.

One of the first section and the third section can include a braided mesh. The other of the third section and the first section can include a laser cut stent. In some examples, the second section can also include the braided mesh. The braided mesh of the second section can have a first plurality of looped ends. The laser cut stent can include a second plurality of looped ends. At least a portion of the first plurality of looped ends can be interwoven with at least a portion of the second plurality of looped ends. Another attachment mechanism to attach the laser cut stent to the braided mesh includes a clip having an outer strut member and a center strut member. The outer strut member can be positioned at one side of the braided mesh, and the center strut member can be positioned at the other side of the braided mesh. The outer strut member and the center strut member can be attached at a securing location to permanently connect the stent to the braided mesh.

The second section can include an anti-thrombogenic coating. The coating proximate the aneurysm neck can help prevent in-implant stenosis.

Another object of the present invention is to provide a method for delivering a flow diverter. The method can include deploying, via a catheter, a first section of a flow diverter through a vessel and distal to an aneurysm neck. The method can include deploying inverting a second section of the flow diverter, causing the second section to contact an inner lumen of the first section. The method can include positioning the second section of the flow diverter such that the second section traverses the aneurysm neck. The method can include moving the catheter proximal to the aneurysm neck and, concurrently, deploying a third section of the flow diverter via the catheter. The method can include creating an overlapping section of the flow diverter proximate the aneurysm neck, the overlapping section comprising at least a portion of the first section, the second section, and the third section.

The first section, the third section, and the second section can include a braided mesh comprising a porosity of from approximately 80% to approximately 90%. The step of creating an overlapping section can decrease the porosity of the flow diverter proximate the overlapping section to from between approximately 50% to approximately 70%.

At least one of the first section or the third section can include a laser cut stent. The second section can include a braided mesh connected to the laser cut stent. The method can include folding the flow diverter at a connection between the braided mesh and the laser cut stent.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is a side view illustration of a flow diverter in a delivery configuration, according to aspects of the present disclosure;

FIGS. 2A and 2B illustrate a flow diverter in an implanted configuration, according to aspects of the present disclosure;

FIG. 4C is a side view illustration of a flow diverter with inflection points between the first, second, and third section, according to aspects of the present disclosure;

FIGS. 5A-5D are side view illustrations of mechanisms for attaching a braided mesh section of a flow diverter to a stent section of the flow diverter, according to aspects of the present disclosure;

FIG. 7 is a flow diagram illustrating a method for implanting a foldable flow diverter, according to aspects of the present disclosure.

DETAILED DESCRIPTION

Figure 3A:
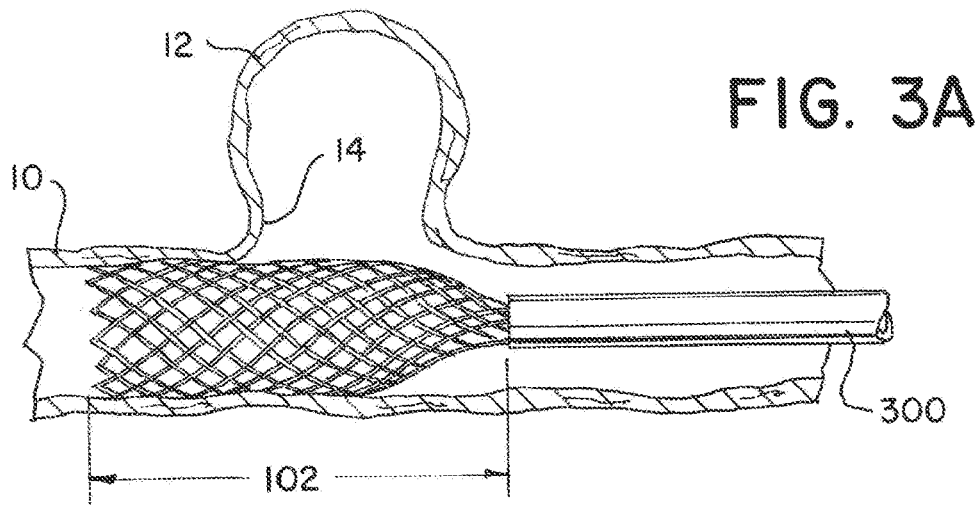
FIGS. 3A-3F are illustrations of example steps for implanting a flow diverter, according to aspects of the present disclosure.

In known treatments of wide neck aneurysms, the aneurysm is typically treated by placing embolic coils within the aneurysm sac and placing a stent within the parent blood vessel across the aneurysm neck. The stent is used in many cases to inhibit the embolic coils from entering the parent blood vessel. If embolic coils enter the parent blood vessel, the coils can obstruct the vessel and/or clots can form on the coils within the blood vessel and create an obstruction in the parent blood vessel. Braided aneurysm implants can be used to treat wide neck aneurysms in lieu of embolic coils. To achieve the forces necessary to anchor braided implants in a wide neck bifurcation, a balance must be made between stiffness and porosity. A braid should have sufficient stiffness so as to maintain an implanted shape and to not collapse within the vessel. The stiffness can be increased by increasing the material density of the flow diverter, or, in other words, decreasing the porosity of the implant.

However, increasing the stiffness by decreasing the porosity can cause a few additional problems. First, increasing the stiffness can cause the implant to be more difficult to move into position through highly tortuous anatomy. Second, decreasing the porosity can also decrease the effectiveness of the porous implant as it relates to occluding an aneurysm. For example, a braided implant can be used to bridge an aneurysm, such that the flow of blood passes through the implant but flow into the aneurysm is inhibited. To further inhibit the flow into the aneurysm, the porosity of the mesh can be decreased.

Yet, therein lies another issue with porosity of braided implants: if the porosity is overly low, then there is a risk that the implant can occlude side branching vessels proximate to the implant. It has been shown that a porosity of approximately 70% is dense enough to treat the aneurysm, yet porous enough to not occlude side branching vessels. To this end, prior art braided implants typically have a porosity of around 70%. These prior designs for braids can be difficult to deliver in a microcatheter especially in highly tortuous anatomy, or they require large size microcatheters to pass to the implant site.

An aspect of the present disclosure is to provide a solution to the aforementioned issues. In particular, the present devices, systems, and methods describe a solution that enables the implant to have a lower overall porosity than prior implant designs. The lower porosity enables the implant to be positioned into the treatment site more easily than in prior designs and further reduces the risk of occluding side branching vessels. However, the presently described devices, systems, and methods do not decrease the effectiveness of the implant as it relates to inhibiting blood flow into an aneurysm. To achieve this, the present devices, systems, and methods describe multi-layer folding flow diverters that provide an overlapping section of the implant proximate the aneurysm when implanted.

Aspects of the present inventions include an implant that is foldable from a delivery configuration to an implanted configuration. In a delivery configuration, the implant can have an elongated tubular form. The implant can then be folded such that a middle section, i.e., the second section described below, is sandwiched between two end sections (i.e., the first and third sections below). When used herein, the terms "tubular" and "tube" are to be construed broadly and are not limited to a structure that is a right cylinder or strictly circumferential in cross-section or of a uniform cross-section throughout its length. For simplicity, tubular structures are generally illustrated herein as having a substantially right cylindrical structure. However, a tubular structure can have a tapered or curved outer surface without departing from the scope of the present invention.

Various devices, systems, and methods are disclosed for providing folding flow diverters, and examples of the devices, systems, and methods will now be described with reference to the accompanying figures. FIG. 1 is a side view illustration of a flow diverter 100 in a delivery configuration, according to aspects of the present disclosure. The flow diverter 100 can have an elongated tubular shape, as shown in the figure, defined by three sections. The first section 102 and third section 106 can be at the ends of the flow diverter 100, while the second section 104 is disposed between the first section 102 and the third section 106. As will be described in greater detail below with reference to FIG. 2A, in an implanted configuration, the third section 106 can overlap a portion of the first section 102, thereby causing the second section 104 to be positioned between the two end sections.

The flow diverter 100 can include a braided mesh 108. The braided mesh 108 can include a number of strands, for example, from about 4 to about 96 strands, each extending from the distal end of the first section 102 to the proximal end of the third section 106. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The strands can wrap helically around the circumference of the flow diverter (or the outer layers 204,206,208 described below with reference to FIGS. 2A and 2B). The number of strands, angle of strands, diameter of the strands, material of strands, and material properties of strands, can all be factors in controlling material properties of the braided mesh 108, including porosity and flexibility. For example, pores 110 are defined by the absence of strand material. When reference is made to porosity herein, it will be understood to mean the percentage of surface area of the implant that is defined by the pores 110 in the braided mesh 108. To illustrate, if the pores 110 of the flow diverter 100 define 10% of the outer surface of the implant, that implant is said to have a 10% porosity.

Referring again to the braided mesh 108, braid strands can be woven such that about half of the strands wrap in a clockwise helix, the other half wraps in a counterclockwise helix, and the oppositely wrapping strands cross over and under each other in an alternating fashion. Constructed as such, portions of the braid having a higher braid angle can therefore have a higher density of strands compared to portions of the braid having lower braid angle. Higher strand density can result in a denser, stiffer braid portion. The braid angles are described in greater detail below with reference to FIG. 4A.

The strands can be made from multiple alloys such as a nickel-titanium alloy, cobalt chromium alloys, platinum, nitinol, stainless steel, tantalum, or other alloys, or any other suitable biocompatible materials or combination of these materials. Also, the material(s) used to make the braided mesh 108 can be absorbable or non-absorbable by the patient over time. Some or all of the braided mesh 108 can be a multi-filament cylindrical mesh made preferably of nitinol with interwoven platinum filaments for radiopacity or Drawn Filled Tube (DFT) Nitinol with about 10% to about 40% platinum.

The second section 104 can have an anti-thrombogenic coating to prevent in-implant stenosis. For instance, the second section 104 can be coated with anti-thrombogenic coating such as Heparin, Phosphorylcholine, a hydrophilic coating, or other such coating as would be appreciated and understood by a person of ordinary skill in the art.

FIGS. 2A and 2B illustrate a flow diverter 100 in an implanted configuration, according to aspects of the present disclosure. FIG. 2A is a partial cross-sectional side view, and FIG. 2B is a cross sectional end view showing an overlapping section 202. In the implanted configuration, the second section 104 can be overlapped by at least a portion of the first tubular section 102 and the third section 106, thereby creating an overlapping section 202 proximate the second section 104. This overlapping section 202 can be placed at the position of the aneurysm neck when the flow diverter 100 is implanted.

Each of the three sections 102,104,106 of the flow diverter 100 described above can include an outer layer defining the tubular structure of the implant. The first section 102 can include a first outer layer 204, the second section 104 can include a second outer layer 206, and the third section 106 can include a third outer layer 208. As the flow diverter 100 is folded from a delivery configuration (as shown in FIG. 1) into an implanted configuration, the second outer layer 206 can be folded to contact the first outer layer 204, and the third outer layer 208 can be folded to contact the second outer layer 206, thereby creating the overlapping section 202. The second section 104 and at least a portion of the third section 106 will be positioned within an inner lumen 112 defined by the first outer layer 204 of the first section 102.

As described above, an object of the present disclosure is to provide a flow diverter 100 that is both easy to implant through a microcatheter and is effective at occluding the aneurysm. The foldable design of the present flow diverter 100 enables these two attributes by having the overlapping section 202. Referring to FIG. 1 for illustration, the braided mesh 108 material of the flow diverter 100 according to the present design can have a porosity significantly higher than previous flow diverter designs. For example, instead of a porosity of 70% (as found in prior designs) the first section 102, second section 104, and/or third section 106 can all have a porosity of greater than 70%, for example from approximately 80% to approximately 90%. This high porosity of can enable the flow diverter 100 to be delivered through a microcatheter or other access sheath more easily.

The section of the flow diverter proximate the aneurysm can have a lower porosity than any section alone, however. When the flow diverter 100 is folded into an implanted configuration, the three-layer shape of the overlapping section 202 can have a lower porosity than any non-overlapping section. This is because the material density of the flow diverter 100 can be additive, and when multiple layers of braided mesh 108 are stacked upon each other, the individual strands of the braid can interfere to decrease the porosity. The overlapping section 202 (comprising the second outer layer 206 and a portion of the first outer layer 204 and third outer layer 208) can have an overall porosity of from approximately 50% to approximately 70%, which, as described above, is sufficient to inhibit blood flow into the aneurysm. The positioning of the overlapping section 202 proximate the aneurysm is described in greater detail below with reference to FIGS. 3A-3F.

Figure 3B:
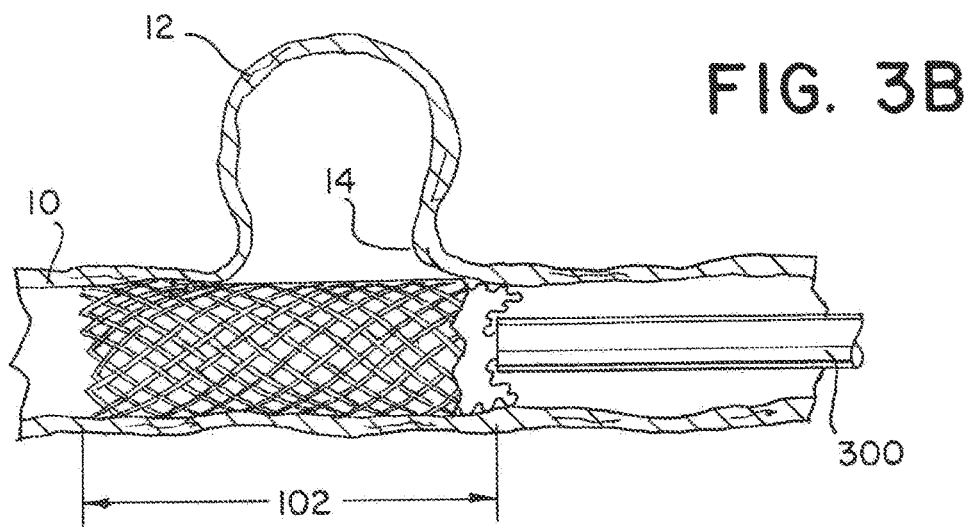

FIGS. 3A-3F are illustrations of example steps for implanting a flow diverter 100, according to aspects of the present disclosure. In FIG. 3A, the distal section (e.g., the first section 102) can be deployed to a treatment site, such as a vessel proximate an aneurysm 12. The distal end of the first section 102 can be placed distal to the aneurysm neck 14. In FIG. 3B, once the first section 102 is deployed distal to the aneurysm neck 14, a microcatheter 300 (or a delivery wire) can be used to invert the flow diverter 100. Inverting the flow diverter 100 can include pushing the microcatheter 300 into the inner lumen 112 defined by the first section 102 while simultaneously deploying the second section 104 of the flow diverter 100.

Figure 3C:
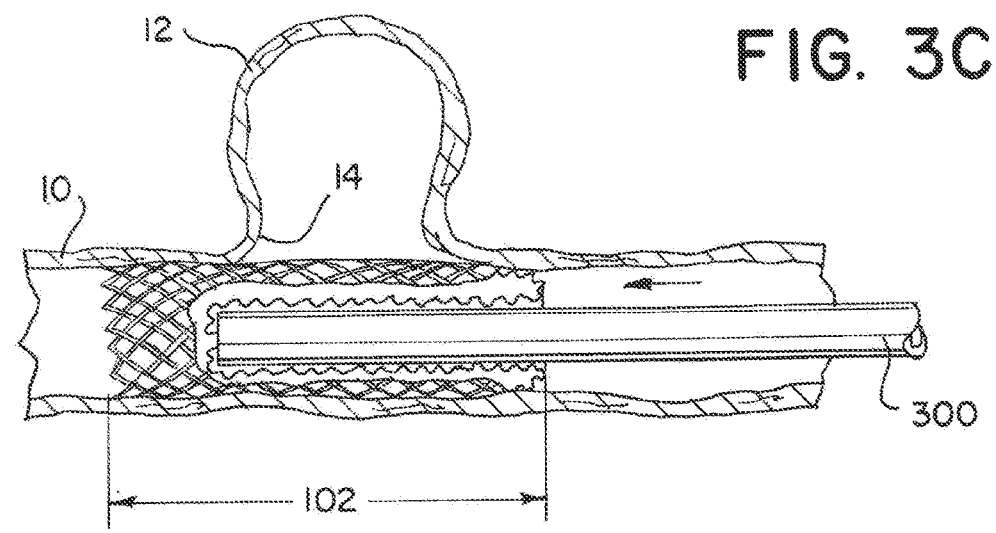
Figure 3D:
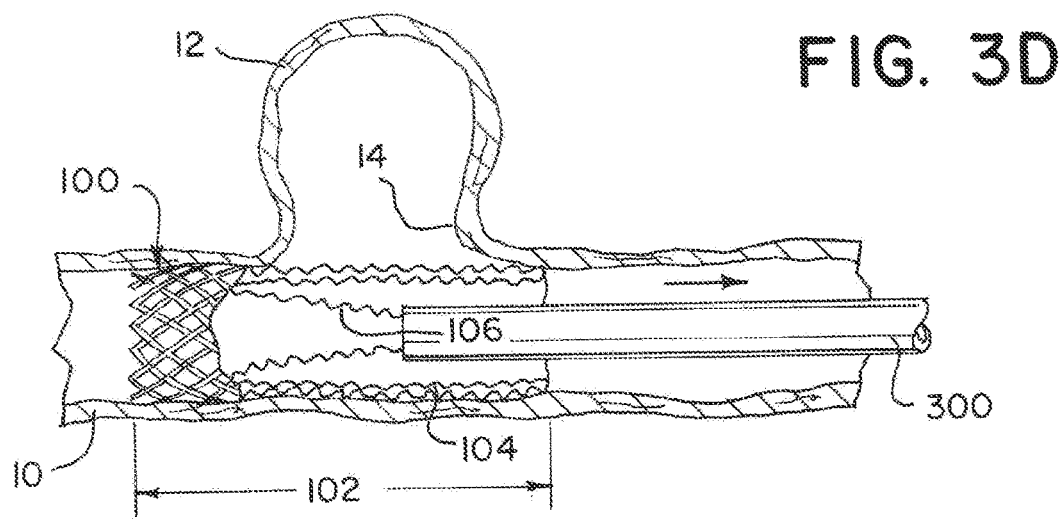
Figure 3E:
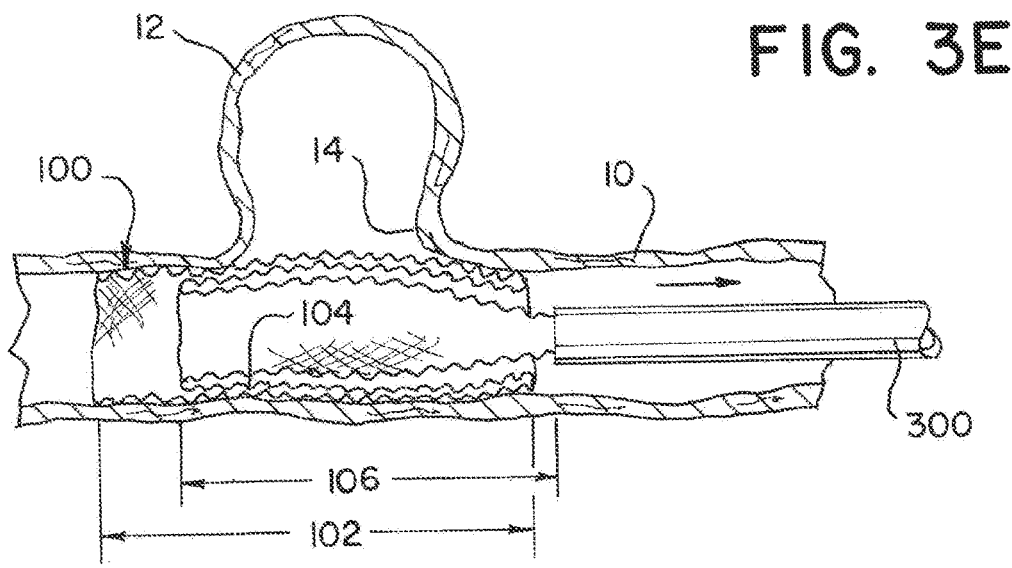
Figure 3F:
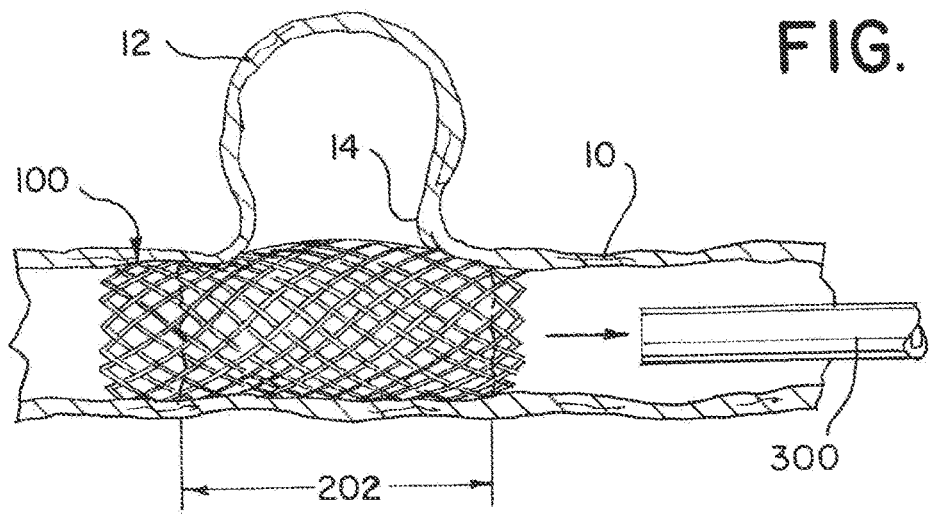

In FIG. 3C, the second section 104 of the flow diverter can be deployed as the microcatheter 300 is advanced distally through the inner lumen 112 of the first section 102. Once the second section 104 is fully deployed into the inner lumen 112 of the first section 102, the microcatheter 300 can be pulled proximally. In FIG. 3D, the microcatheter 300 is pulled proximally while the third section 106 is simultaneously deployed. In FIG. 3E, the microcatheter 300 is further retracted proximally and proximal to the aneurysm neck 14 as the third section 106 continues to be deployed. In FIG. 3F, the microcatheter 300 is retracted from the treatment site, and the first section 102, second section 104, and third section 106 overlap to form the overlapping section 202, which bridges the aneurysm neck 14.

Figure 4A:
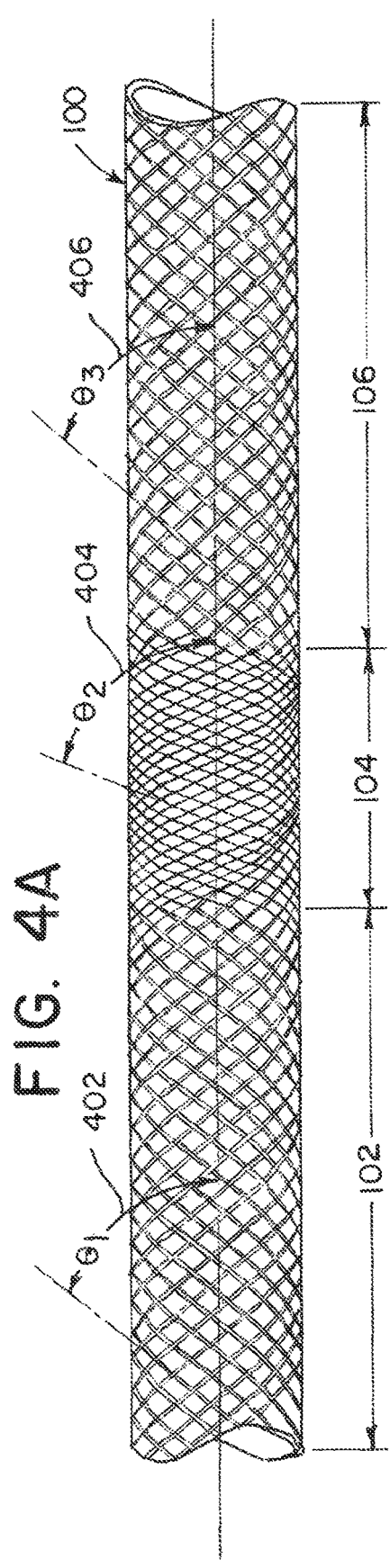
FIG. 4A is a side view illustration of a flow diverter having a second section with a different braid angle than a first and third section, according to aspects of the present disclosure.
Figure 4B:
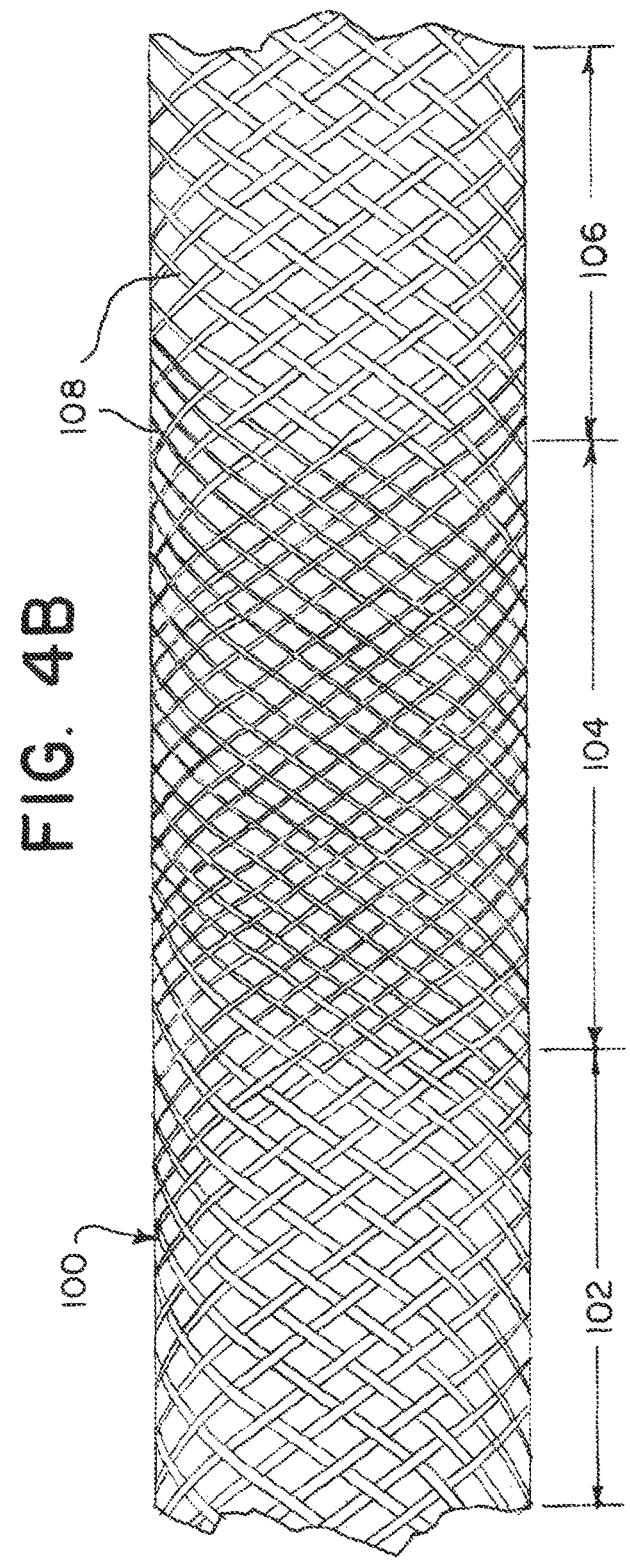
FIG. 4B is a side view illustration of a flow diverter having a second section with a thinner material than a first and third section, according to aspects of the present disclosure.

FIGS. 4A-4C are illustrations of example designs to help facilitate the folding of the foldable flow diverter 100. FIG. 4A is a side view illustration of a flow diverter 100 having a second section 104 with a different braid angle 404 than a first section 102 and third section 106, according to aspects of the present disclosure. Stiffness of the flow diverter 100 can be determined at least in part by braid angle (e.g., braid angles 402, 404, 406 in FIG. 4A). For ease of discussion, weaker, more flexible portions of braid can have a lower braid angle compared to stronger, stiffer portions of the braid; however, weaker and stiffer portions of the braids can differ in strand diameter, number of strands, material of strands, be treated to have differing stiffness/flexibility, and/or by other means as would be appreciated and understood by a person of ordinary skill in the art.

In the single layer tubular shape illustrated in FIG. 4A, the braided mesh 108 can have a circumference C that is substantially uniform along the length L when the flow diverter 100 is in a delivery configuration. The tubular shape can have a central axis A extending along the length of the braided mesh 108. The one or more braid angles 402, 404, 406 (shown in the figure as angles $\theta_1$, $\theta_2$, $\theta_3$) can be measured by comparing the tangential trajectory of a braid strand to the central axis A, as illustrated and as would otherwise be understood by a person of ordinary skill in the art according to the teachings herein. Sections of the implant with higher braid angles, such as the second braid angle 404 shown in the example in FIG. 4A, can have a lower overall porosity and can be relatively stiffer than sections having a lower braid angle.

As shown in FIG. 4A, different sections of the flow diverter 100 can have different braid angles. For example, the second section 104 can have a second braid angle 404 at an angle $\theta_2$, the first section 102 can have a first braid angle 402 at an angle $\theta_1$, and the third section 106 can have a third braid angle 406 at an angle $\theta_3$. The angles $\theta_1$, $\theta_2$, $\theta_3$ can all be different braid angles, or one or more of the sections can have the same braid angle. For example, it is contemplated that the first braid angle 402 and the third braid angle 406 are the same angle, while the second braid angle 404 is different than that of the first braid angle 402 and the third braid angle 406.

The second braid angle 404 can be a higher angle than the first braid angle 402 and the third braid angle 406 (e.g., $\eta_2$ is a higher angle than $\theta_1$ and $\theta_3$). This, of course, can also mean that the second section 104 is less porous than the first section 102 and the third section 106. In this design, the center of the flow diverter 100, for example the overlapping section 202 when in an implanted configuration, can have a significantly lower porosity than the ends of the implant. This can be beneficial to the construct, because the overlapping section 202 is to be implanted to inhibit blood flow into the aneurysm. Having the lowest porosity/highest braid density near the aneurysm neck can achieve this goal. In other examples, the second braid angle 404 can be a lower angle than the first braid angle 402 and the third braid angle 406 (e.g., $\eta_2$ is a lower angle than $\theta_1$ and $\theta_3$). This, of course, can also mean that the second section 104 is more porous than the first section 102 and the third section 106. This design can enable the second section 104 to be less stiff than the end sections, thereby facilitating the folding of the flow diverter 100. The overlapping section 202 can still have a lower porosity than any of the sections alone, however. This is because, as described above, the overlapping section 202, when in an implanted configuration, includes the three-layer construct, which can have a lower overall porosity.

FIG. 4B is a side view illustration of a flow diverter 100 having a second section 104 with a thinner material than the first section 102 and the third section 106, according to aspects of the present disclosure. The second section 104 of a flow diverter can have a thinner material than the end sections (e.g., the first section 102 and the third section 106). This can be created by having strands of the braided mesh 108 that are smaller in diameter in the second section 104. This can facilitate the folding of the second section 104 into the inner lumen defined by the first section 102.

FIG. 4C is a side view illustration of a flow diverter 100 with inflection points 408,410 between the first section 102, second section 104, and third section 106, according to aspects of the present disclosure. Inflection points 408,410 can be positioned between adjacent sections 102,104,106 so as to facilitate the folding of the flow diverter 100 from the delivery configuration to the implanted configuration. For example, a first inflection point 408 can be positioned between the first section 102 and the second section 104, and a second inflection point 410 can be positioned between the second section 104 and the third section 106. The inflection points 408,410 can be a section of the braided mesh 108 that is weaker than the rest of the braid. This weaker section can be created by flattening, indenting, or thinning the wire of the braid at that section.

FIGS. 5A-5D are side view illustrations of mechanisms for attaching a braided mesh 108 section of a flow diverter 100 to a stent 502 section of the flow diverter 100, according to aspects of the present disclosure. In these examples, one or more of the end sections (e.g., the first section 102 and/or the third section 106) can be a stent 502 material instead of a braided mesh 108. With this construct, the flow diverter 100 can fold at a connection point between the braided mesh 108 section and the stent 502 section. As will be appreciated, laser cut stents 502 can be stiffer than a braided mesh 108 and exert a greater outward, radial force on the surrounding vasculature, thereby both anchoring the implant into position and ensuring the vessel does not collapse. In these examples, the second section 104 can maintain the braided mesh 108 material such that the second section 104 can fold, as described above.

Although FIGS. 5A and 5B show the third section 106 including the stent 502 portion of the implant, the first section 102 and/or the third section 106 can include the stent 502 portion. This is shown in greater detail below with reference to FIGS. 6A-6C. Furthermore, the shape and/or design of the stent 502 is not limited to the examples shown in FIGS. 5A and 5B, which are merely illustrative. FIG. 5A depicts a stent 502 having a series of peaks and troughs connected together, while FIG. 5B depicts a stent 502 having a uniform pattern of interconnected shapes. The stent 502 can have a laser cut lattice design, a shape set wire design, a wire braid design, and/or the like.

FIGS. 5C and 5D depict example attachment mechanisms for connecting a braided mesh 108 section of the implant to a stent 502 section of the implant. As shown in FIG. 5C, the braided mesh 108 of the second section 104, for example, can include a first plurality of looped ends 504. The laser cut stent 502 section can include a second plurality of looped ends 506. At least a portion of the first plurality of looped ends 504 can be interwoven with at least a portion of the second plurality of looped ends 506 to connect the braided mesh 108 to the stent 502.

In other examples, a clip 550 can be used to connect the braided mesh 108 to the stent 502. This clip 550 mechanism is described in greater detail in U.S. Pat. No. 10,076,428, which is herein incorporated by reference as if fully set forth below. The clip 550 can be connected to the end of the stent 502 and can include a center strut member 552 and an outer strut member 554. The center strut member 552 can be positioned at one side (one surface) of the braided mesh 108, while the outer strut member 554 can be positioned at the other side (other surface) of the braided mesh 108. A securing location 556 can be positioned where the center strut member 552 and the outer strut member 554 meet. At this securing location 556, the center strut member 552 can be permanently connected to the outer strut member 554 via one or more welds, soldered connections, chemical adhesives, and or the like. Once permanently connected, the stent 502 can be secured to the braided mesh 108.

Figure 6A:
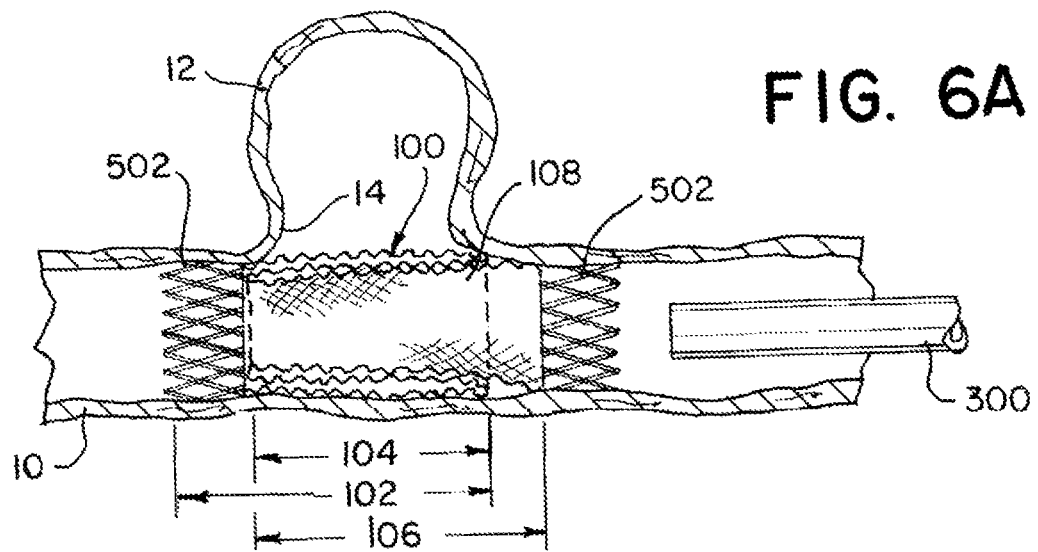
FIGS. 6A-6C are cross-sectional schematics of implanted flow diverters having both braided mesh sections and stent sections, according to aspects of the present disclosure.
Figure 6B:
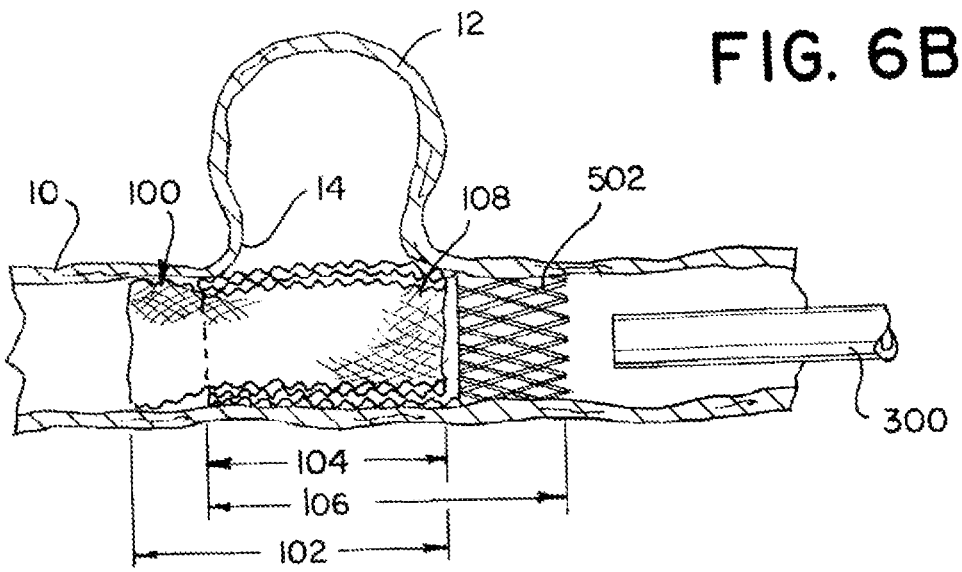
Figure 6C:
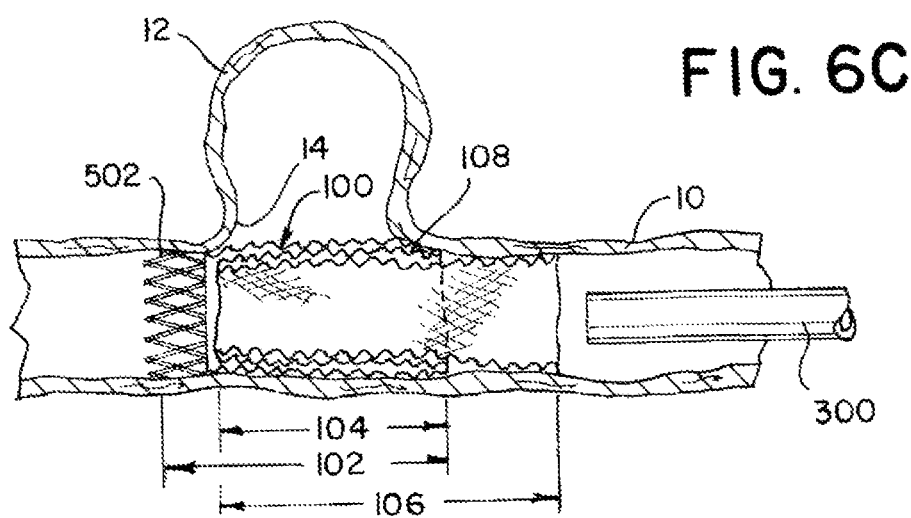

FIGS. 6A-6C are cross-sectional schematics of implanted flow diverters 100 having both braided mesh 108 sections and stent 502 sections, according to aspects of the present disclosure. As described above, the stent section 502 of an implant can be located at the first section 102 of the implant, at the third section 106 of the implant, or at both the first section 102 and the third section 106. In FIG. 6A, the stent 502 is positioned at both the first section 102 and the third section 106. The folding of the flow diverter 100 can still be facilitated by the second section 104 containing the less-stiff braided mesh 108. In FIG. 6B, the first section 102 of the implant includes the stent 502; in FIG. 6C, the third section 106 of the implant includes the stent 502.

FIG. 7 is a flow diagram illustrating a method 700 for implanting a foldable flow diverter, according to aspects of the present disclosure. The method steps in FIG. 7 can be implemented by any of the example means described herein or by similar means, as will be appreciated. Referring to method 700 as outlined in FIG. 7, in step 705, a first section of a flow diverter can be deployed via a catheter, such as a microcatheter. The first section can be delivered through a vessel and distal to an aneurysm neck. In step 710, a second section of the flow diverter can be inverted, causing the second section to contact an inner lumen of the first section.

In step 715, the second section can be positioned such that the second section traverses the aneurysm neck. In step 720, the catheter can be moved (i.e., retracted) proximal to the aneurysm neck. Concurrently with moving the catheter, a third section of the flow diverter can be deployed via the catheter. In step 725, an overlapping section proximate the aneurysm neck can be created including at least a portion of the first section, the second section, and the third section.

Method 700 can end after step 725. In other examples, additional steps according to the examples described above can be performed. For example, the step of creating an overlapping section can decrease the porosity of the flow diverter proximate the overlapping section to from between approximately 50% to approximately 70%. In some examples, method 700 can include folding the flow diverter at a connection between a braided mesh section of the implant and a laser cut stent section of the implant.

The descriptions contained herein are examples of embodiments of the invention and are not intended in any way to limit the scope of the invention. The invention contemplates many variations and modifications of the implant, including: alternative delivery methods, alternative braid materials, alternative means for achieving a desired stiffness/flexibility of braid material, additional structures affixed to the implant (e.g. to aid in anchoring the implant, blood flow diversion, embolism formation, etc.), alternative predetermined braid shapes (e.g. one inversion, three inversions, four inversions, five or more inversions, non-radially symmetric shapes, alternative segment shapes, etc.), alternative implanted shapes, etc. Modifications apparent to one of ordinary skill in the art following the teachings of this disclosure are intended to be within the scope of the claims which follow.

What is claimed is:

1. A vascular flow diverter, comprising:
a first tubular section defining an inner lumen;
a third tubular section positionable within the inner lumen; and
a second tubular section disposed between the first tubular section and the third tubular section,
wherein the vascular flow diverter is foldable from a delivery configuration to an implanted configuration,
wherein, in the delivery configuration, the first tubular section, the second tubular section, and the third tubular section define a single-layer cylindrical shape, and
wherein, in the implanted configuration, the second tubular section is overlapped by at least a portion of the first tubular section and the third tubular section, thereby creating a three-layer shape proximate the second tubular section,
wherein the first tubular section, the third tubular section, and the second tubular section comprise a braided mesh comprising a porosity of from approximately 80% to approximately 90%, and
wherein three-layer shape proximate the second tubular section comprises a porosity of from approximately 50% to approximately 70%.

2. The vascular flow diverter of claim 1, wherein the second tubular section comprises a different porosity than the first tubular section and the third tubular section.

3. The vascular flow diverter of claim 1, wherein:
the first tubular section, the third tubular section, and the second tubular section each comprise a braided mesh; and
the braided mesh of the second tubular section comprises a different braid angle than the braided mesh of the first tubular section and the third tubular section.

4. The vascular flow diverter of claim 1, wherein:
the second tubular section comprises a first material thickness;
the first tubular section and the third tubular section comprise a second material thickness; and
the first material thickness is less than the second material thickness.

5. The vascular flow diverter of claim 1, further comprising:
a first inflection point disposed between first tubular section and the second tubular section; and
a second inflection point disposed between third tubular section and the second tubular section.

6. The vascular flow diverter of claim 1, wherein:
one of the first tubular section and the third tubular section comprises a braided mesh; and
the other of the third tubular section and the first tubular section comprises a laser cut stent.

7. The vascular flow diverter of claim 1, wherein the second tubular section comprises an anti-thrombogenic coating.

8. An implant shapeable to a cylindrical shape and movable to an implanted shape, the implant comprising:
a first section comprising a first outer layer, the first section comprising a porosity of from approximately 80% to approximately 90%;
a second section comprising a second outer layer foldable to contact the first outer layer the second section comprising a porosity of from approximately 80% to approximately 90%; and
a third section comprising a third outer layer foldable to contact the second outer layer, the third section comprising a porosity of from approximately 80% to approximately 90%,
wherein, when in the implanted shape, the implant comprises a three-layer overlapping section comprising the first outer layer, the second outer layer, and the third outer layer,
wherein, when in the implanted shape, the three-layer overlapping section is disposed proximate an aneurysm neck, and
wherein, when in the implanted shape, the three-layer overlapping section comprises a porosity of from approximately 50% to approximately 70%.

9. The implant of claim 8, wherein:
the first section, the third section, and the second section each comprise a braided mesh; and
the braided mesh of the second section comprises a different braid angle than the braided mesh of the first section and the third section.

10. The implant of claim 8, further comprising:
a first inflection point disposed between first section and the second section; and
a second inflection point disposed between third section and the second section.

11. The implant of claim 8, wherein:
one of the first section and the third section comprises a braided mesh; and
the other of the third section and the first section comprises a laser cut stent.

12. The implant of claim 11, wherein:
the second section comprises the braided mesh;
the braided mesh of the second section comprises a first plurality of looped ends;
the laser cut stent comprises a second plurality of looped ends; and
at least a portion of the first plurality of looped ends are interwoven with at least a portion of the second plurality of looped ends.

13. The implant of claim 8, wherein the second section comprises an anti-thrombogenic coating.

14. An implant shapeable to a cylindrical shape and movable to an implanted shape, the implant comprising:
a first section comprising a first outer layer;
a second section comprising a second outer layer foldable to contact the first outer layer, the second section comprising a braided mesh comprising a first plurality of looped ends; and
a third section comprising a third outer layer foldable to contact the second outer layer,
wherein, when in the implanted shape, the implant comprises a three-layer overlapping section comprising the first outer layer, the second outer layer, and the third outer layer,
wherein, when in the implanted shape, the three-layer overlapping section is disposed proximate an aneurysm neck,
wherein one of the first section and the third section comprises the braided mesh, and the other of the third section and the first section comprises a laser cut stent,
wherein the laser cut stent comprises a second plurality of looped ends, and wherein at least a portion of the first plurality of looped ends are interwoven with at least a portion of the second plurality of looped ends.

15. The implant of claim 14, wherein the first section, the third section, and the second section comprise a braided mesh comprising a porosity of from approximately 80% to approximately 90%.

16. The implant of claim 15, wherein, when in the implanted shape, the three-layer overlapping section comprises a porosity of from approximately 50% to approximately 70%.

* * * * *